(12) United States Patent
Dinsmore (10) Patent No.: US 6,658,086 B2
(45) Date of Patent: Dec. 2, 2003

(54) OPTICALLY DRIVEN THERAPEUTIC RADIATION SOURCE WITH VOLTAGE GRADIENT CONTROL

(75) Inventor: Mark Dinsmore, Sudbury, MA (US)

(73) Assignee: Carl Zeiss, Oberkochen (DE)

( * ) Notice: Subject to any disclaimer, the term of this patent is extended or adjusted under 35 U.S.C. 154(b) by 0 days.

(21) Appl. No.: 10/175,164

(22) Filed: Jun. 19, 2002

(65) Prior Publication Data

US 2002/0196900 A1 Dec. 26, 2002

Related U.S. Application Data

(60) Provisional application No. 60/299,204, filed on Jun. 19, 2001.

(51) Int. Cl.[7] ................................................. A61N 5/10
(52) U.S. Cl. ......................................... 378/65; 378/119
(58) Field of Search ........................... 378/65, 119, 136, 378/64

(56) References Cited

U.S. PATENT DOCUMENTS

| | | | |
|---|---|---|---|
| 5,090,043 A | 2/1992 | Parker et al. | |
| 5,153,900 A | 10/1992 | Nomikos et al. | |
| RE34,421 E | 10/1993 | Parker et al. | |
| 5,369,679 A | 11/1994 | Sliski et al. | |
| 5,422,926 A | 6/1995 | Smith et al. | |
| 5,428,658 A | 6/1995 | Oettinger et al. | |
| 5,504,799 A | 4/1996 | Suzuki | |
| 5,621,780 A | 4/1997 | Smith et al. | |
| 6,148,061 A | 11/2000 | Shefer et al. | |
| 6,195,411 B1 * | 2/2001 | Dinsmore | 378/65 |
| 6,319,188 B1 | 11/2001 | Lovoi | |
| 6,320,932 B2 * | 11/2001 | Dinsmore | 378/65 |
| 6,320,935 B1 | 11/2001 | Shinar et al. | |
| 6,324,257 B1 | 11/2001 | Halavee | |
| 6,480,568 B1 * | 11/2002 | Dinsmore | 378/65 |

FOREIGN PATENT DOCUMENTS

WO   WO 01/47596   7/2001

* cited by examiner

Primary Examiner—David V. Bruce
Assistant Examiner—Irakli Kiknadze
(74) Attorney, Agent, or Firm—McDermott, Will & Emery (57) ABSTRACT

A miniaturized, optically driven, therapeutic radiation source is disclosed in which the voltage gradient between a high electron accelerating voltage and the ground potential can be controlled. The electron source and the target element are disposed within a capsule which defines a substantially evacuated region extending along an electron beam axis. The inner surface of the capsule is coated with a weakly conductive or semiconductive coating, so that a substantially uniform voltage gradient is maintained within the evacuated capsule. In this way, the chances of electric flashover or breakdown are reduced. Also, secondary emissions of electrons striking the inner wall of the capsule are reduced. X-ray production efficiency is optimized by maximizing the percentage of electrons propagated directly to the target.

24 Claims, 5 Drawing Sheets

OPTICALLY DRIVEN THERAPEUTIC RADIATION SOURCE WITH VOLTAGE GRADIENT CONTROL

CROSS-REFERENCE TO RELATED APPLICATIONS

This application claims benefit of U.S. Provisional Application Ser. No. 60/299,204, entitled "Optically Driven Therapeutic Radiation Source With Voltage Gradient Control" and filed on Jun. 19, 2001.

FIELD OF THE INVENTION

The present invention relates to therapeutic radiation sources, and in particular to miniaturized, highly efficient, optically-driven therapeutic radiation sources.

BACKGROUND OF THE INVENTION

In the field of medicine, therapeutic radiation such as x-ray radiation and γ-ray radiation is used for diagnostic, therapeutic and palliative treatment of patients. The conventional medical radiation sources used for these treatments include large, fixed position machines as well as small, transportable radiation generating probes. The current state-of-the-art treatment systems utilize computers to generate complex treatment plans.

Conventional radiation systems used for medical treatment utilize a high power remote radiation source, and direct a beam of radiation at a target area, such as a tumor inside the body of a patient. This type of treatment is referred to as teletherapy because the radiation source is located a pre-defined distance from the target. This treatment suffers from the disadvantage that tissue disposed between the radiation source and the target is exposed to radiation. Teletherapy radiation sources, which apply radiation to target regions internal to a patient from a source external to the target regions, often cause significant damage not only to the target region or tissue, but also to all surrounding tissue between the entry site, the target region, and the exit site.

Brachytherapy, on the other hand, is a form of treatment in which the source of radiation is located close to or in some cases within the area receiving treatment. Brachytherapy, a word derived from the ancient Greek word for close ("brachy"), offers a significant advantage over teletherapy, because the radiation is applied primarily to treat only a predefined tissue volume, without significantly affecting the tissue adjacent to the treated volume. The term brachytherapy is commonly used to describe the use of "seeds," i.e. encapsulated radioactive isotopes, which can be placed directly within or adjacent the target tissue to be treated. Handling and disposal of such radioisotopes, however, may impose considerable hazards to both the handling personnel and the environment.

The term "x-ray brachytherapy" is defined for purposes of this application as x-ray radiation treatment in which the x-ray source is located close to or within the area receiving treatment. An x-ray brachytherapy system, which utilizes a miniaturized low power radiation source that can be inserted into, and activated from within, a patient's body, is disclosed in U.S. Pat. No. 5,153,900 issued to Nomikos et al., U.S. Pat. No. 5,369,679 to Sliski et al., and U.S. Pat. No. 5,422,926 to Smith et al., all owned by the assignee of the present application, all of which are hereby incorporated by reference.

The x-ray brachytherapy system disclosed in the above-referenced patents includes a miniaturized, insertable probe which is capable of generating x-ray radiation local to the target tissue, so that radiation need not pass through the patient's skin, bone, or other tissue prior to reaching the target tissue. The insertable probe emits low power x-rays from a nominal "point" source located within or adjacent to the desired region to be affected. In x-ray brachytherapy, therefore, x-rays can be applied to treat a predefined tissue volume without significantly affecting the tissue adjacent to the treated volume. Also, x-rays may be produced in pre-defined dose geometries disposed about a predetermined location. X-ray brachytherapy offers the advantages of brachytherapy, while avoiding the use and handling of radioisotopes. Also, x-ray brachytherapy allows the operator to control over time the dosage of the delivered x-ray radiation.

X-ray brachytherapy typically involves positioning the insertable probe into or adjacent to the tumor, or into the site where the tumor or a portion of the tumor was removed, to treat the tissue adjacent the site with a local boost of radiation. X-ray probes of the type generally disclosed in U.S. Pat. No. 5,153,900 include a housing, and a hollow, tubular probe or catheter extending from the housing along an axis and having an x-ray emitting target at its distal end. The probe may enclose an electron source, such as a thermionic cathode. In another form of an x-ray brachytherapy device, as disclosed in U.S. Pat. No. 5,428,658, an x-ray probe may include a flexible probe, such as a flexible fiber optic cable enclosed within a metallic sheath. In such a flexible probe, the electron source may be a photocathode. In a photocathode configuration, a photoemissive substance is irradiated by a LED or a laser source, causing the generation of free electrons. Typically, the flexible fiber optic cable couples light from a laser source or a LED to the photocathode.

It is possible to reduce the power requirements of min-iaturized therapeutic radiation sources used in x-ray brachytherapy, by optically driving the thermionic cathodes in the electron sources, instead of ohmically heating the thermionic cathodes. U.S. patent application Ser. No. 09/884,561 (commonly owned by the assignee of the present application and hereby incorporated by reference) (hereinafter the "'561" application) discloses a miniaturized therapeutic radiation source that includes a reduced-power, increased efficiency electron source that is optically driven. The '561 application discloses an electron source that includes a thermionic cathode having an electron emissive surface. The '561 application discloses using laser energy to heat the electron emissive surface of the thermionic cathode, instead of heating the electron emissive surface of the thermionic emitter using conventional ohmic heating. In this way, electrons can be produced in a quantity sufficient to produce the electron current necessary for generating therapeutic radiation at the target, while significantly reducing the power requirements for the therapeutic devices. Electrons can be generated with minimal heat loss, without requiring a vacuum-fabricated photocathode.

In the devices disclosed in U.S. Pat. Nos. 5,133,900 and 5,428,658, and in the '561 application, the electron source and the target element are enclosed within a substantially rigid capsule. The electron source generates an electron beam along a beam path, and the target element is positioned in the beam path. An accelerating electric field may be established within the capsule. The accelerating electric field acts to accelerate the electrons emitted from the electron source toward the target element. The target element emits therapeutic radiation in response to incident electrons from the electron source.

The capsule defines a substantially evacuated interior region extending along the electron beam axis. Typically, the inner surface of the capsule is lined with an electrical insulator. Although the vacuum is used extensively for the insulation of high voltages in devices such as the x-ray probes described above, the reliability of the vacuum is limited by the operational risk of an unpredictable "sparking" or "arcing" between the electrodes, when the insulating capability of the vacuum gap is suddenly lost and electrical breakdown is said to have occurred. Also, the efficient production of x-rays requires that the electron path be directly from the cathode to the target. If the electrons are deflected to the walls by effects of insulator charging, the efficiency of x-ray production is reduced, and stability of the x-ray output is compromised.

It is therefore important to establish a substantially uniform voltage gradient in the region between the electron source and the target, in order to avoid such electrical breakdown and to maximize and stabilize the x-ray output. It is an object of this invention to provide a high efficiency, miniaturized therapeutic radiation source having a substantially uniform voltage gradient within the vacuum region between the electron source and the target.

SUMMARY OF THE INVENTION

The present invention is directed to a high efficiency, miniaturized, optically driven therapeutic radiation source. The therapeutic radiation source includes an electron source and a target element that generates therapeutic radiation in response to incident accelerated electrons from the electron source. The electron source and the target element are enclosed within an evacuated capsule, whose inner surface is coated with a weakly conductive or semiconductive coating. In this way, chances of flashover and electrical breakdown in the evacuated capsule are substantially reduced, and the electrons are propagated directly from the cathode to the target.

The present invention features a therapeutic radiation source, which includes an optical source, a probe assembly, and a radiation generator assembly. The optical source is preferably a laser, or a light emitting diode. The probe assembly includes an optical delivery structure, such as a fiber optic cable, having a proximal end and a distal end. The fiber optic cable is adapted to transmit optical radiation incident on its proximal end to its distal end, and to direct a beam of optical radiation transmitted therethrough to impinge upon a surface of the thermionic cathode. This beam of optical radiation has a power level sufficient to heat at least a portion of the surface to an electron emitting temperature, so as to cause thermionic emission of electrons from the surface.

The radiation generator assembly includes an electron source, and a target element. The electron source includes a thermionic cathode having an electron emissive surface. The electron source is responsive to optical radiation transmitted to the distal end of the fiber optic cable, to generate an electron beam along a beam path along a nominally straight reference axis. The target element is positioned in the electron beam path. The target element includes at least one x-ray emissive material adapted to emit x-rays in response to incident accelerated electrons from the electron source.

A substantially rigid capsule encloses the electron source and the target element. The capsule defines a substantially evacuated interior region extending along the nominally straight beam axis, between the thermionic cathode at the proximal end of the capsule and a target element at the distal end of the capsule. The total resistance of the inner surface of the capsule is preferably high enough to limit dissipated power to less than 10% total target power.

The invention includes means for providing an accelerating voltage between the electron source and the target element, so as to establish an accelerating electric field which acts to accelerate electrons emitted from the electron source towards the target element. The accelerating voltage has a preselected maximum value.

The inner surface of the evacuated capsule is coated with a weakly conductive or semiconductive coating to provide a substantially smooth voltage gradient within the capsule, between the preselected maximum value and the ground potential. The weakly conductive or semiconductive coating, applied to the inner surface of the capsule, is also adapted to reduce secondary emissions of electrons striking the coated inner surface of the capsule. The weakly conductive or semiconductive coating is further adapted to reduce the electrical field in the vicinity of the triple junction point, thus reducing the possibility of electrical flashover the triple junction point of the thermionic cathode. Sufficient current is carried in the coating to prevent charge buildup from field emission, and subsequent avalanche and breakdown.

DETAILED DESCRIPTION

The present invention is directed to a miniaturized, low power therapeutic radiation source which includes an electron-beam activated therapeutic radiation source, and which uses a laser-heated thermionic cathode. As described in the '561 application, use of a thermionic cathode that is laser-heated significantly reduces the power requirements for such therapeutic radiation sources. The therapeutic radiation source includes an electron source and a target, which are enclosed within an evacuated capsule. The present invention features the use of a weakly conductive or semiconductive coating, applied on the inner surface of the evacuated capsule. In this way, a substantially uniform voltage gradient is established in the region between the electron source and the target, so that high electric field regions or spikes are avoided within the evacuated capsule, the chances of electrical breakdown are reduced, and the electrons propagate directly to the target. The weakly conductive or semiconductive coating also reduces the chances for secondary emissions of electrons that strike the walls of the capsule to cause an avalanche that eventually causes an electrical breakdown. Field emitted currents are swept away, preventing charge-up and breakdown.

Figure 1:
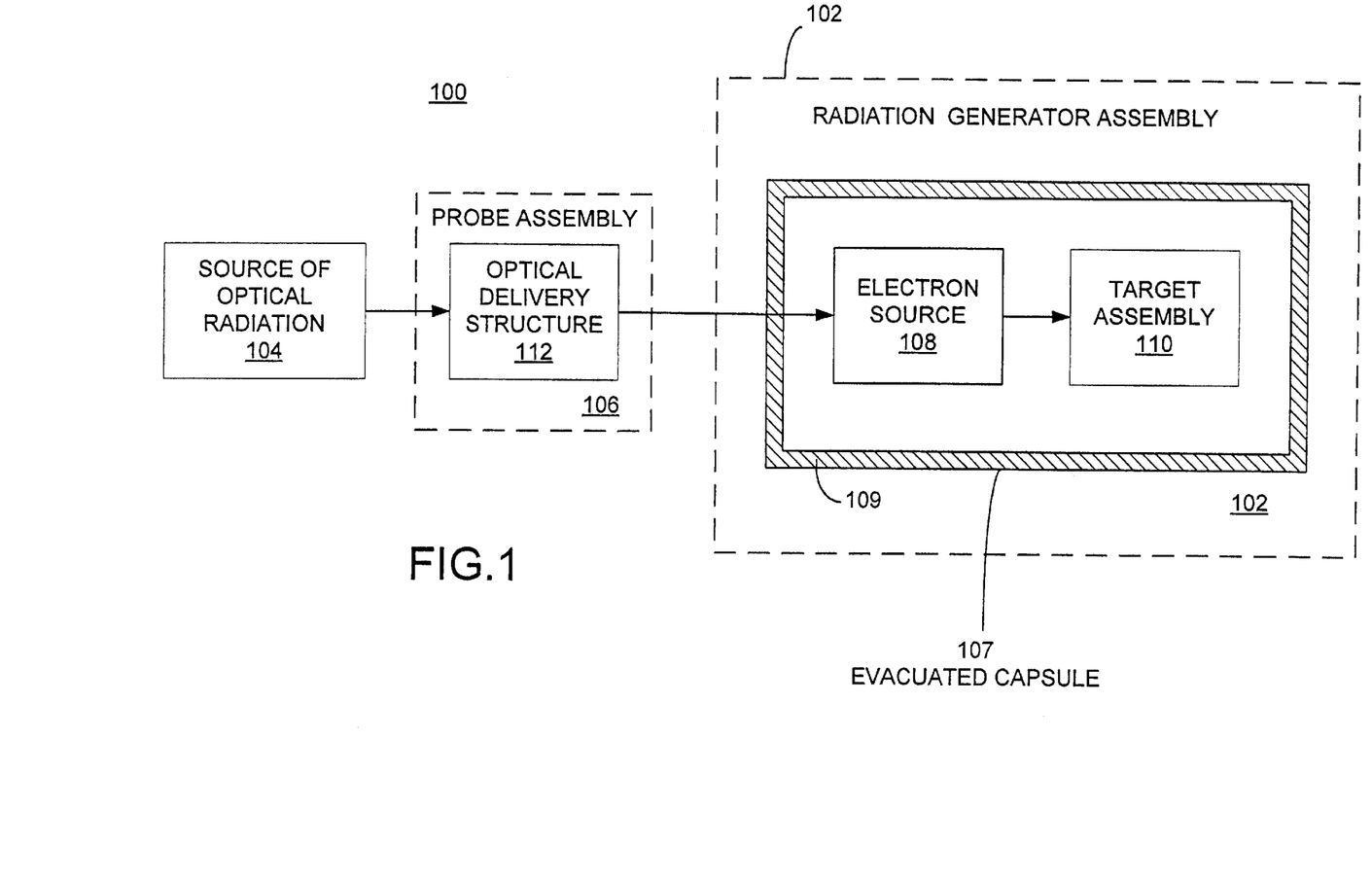
FIG. 1 is a schematic block diagram of an overview of one embodiment of a therapeutic radiation source constructed in accord with the present invention.

FIG. 1 is a schematic block diagram of an overview of one embodiment of a therapeutic radiation source 100, constructed according to the present invention. An electron source 108 and a target assembly 110 are enclosed within an evacuated capsule 107. The interior surface of the capsule is coated with a layer 109 of weakly conductive or semiconductive material. In overview, the system of the present invention includes a radiation generator assembly 102, a source of optical radiation 104, and a probe assembly 106. Preferably, the source of optical radiation 104 is a laser, so that the optical radiation generated by the source is substantially monochromatic, and coherent. The laser may be a NdiYAG laser, by way of example; however other lasers known in the art may be used, such as a diode laser and a molecular laser. Alternatively, other sources of high intensity light may be used, such as LEDs (light emitting diodes).

The radiation generator assembly 102 includes the electron source 108, and the target assembly 110. The target assembly 110 includes means for emitting therapeutic radiation in response to incident accelerated electrons from the electron beam. The probe assembly 106 includes optical delivery structure 112, such as a fiber optical cable. The optical delivery structure 112 directs a beam of laser radiation generated by the laser 104 onto the electron source 108. The laser beam heats the electron source 108, so as to cause thermionic emission of electrons. Within the capsule 107, an accelerating electric field is established which acts to accelerate electrons emitted from the electron source toward the target assembly. The layer 109 of weakly conductive or semiconductive coating is adapted to provide a substantially smooth voltage gradient within the capsule.

Generally, the apparatus of the present invention operates at voltages in the range of approximately 10 keV to 90 keV, and electron beam currents in the range of approximately 1 nA to 100 µA. At those operating voltages and currents, radiation output is relatively low, and the apparatus may be made small enough to be adapted for implantation in medical therapeutic applications. In view of the low-level radiation output, adequate tissue penetration and cumulative dosage may be attained by positioning the radiation source adjacent to or within the region to be irradiated. Thus, therapeutic radiation is emitted from a well-defined, small source located within or adjacent to the region to be irradiated.

Figure 2A:
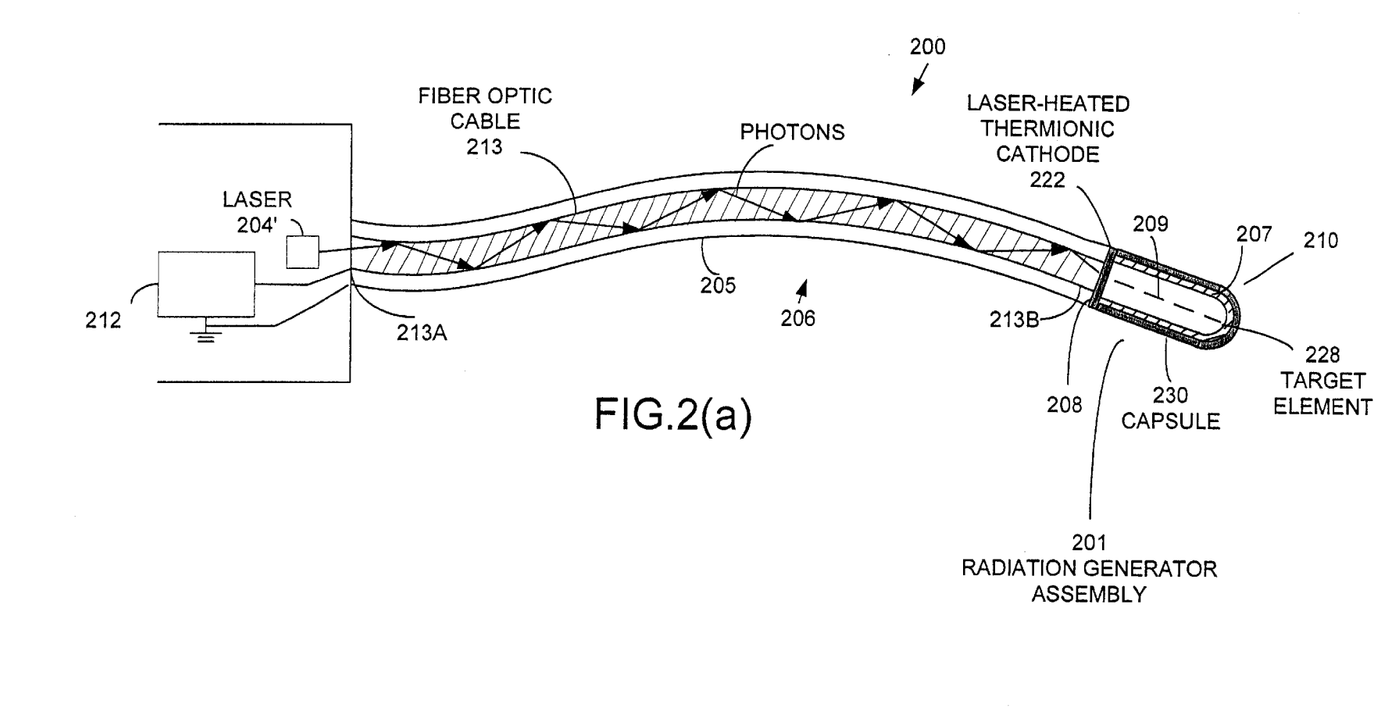
FIG. 2(a) is an overall, diagrammatic view of one embodiment of a therapeutic radiation source constructed according to the present invention.
Figure 2B:
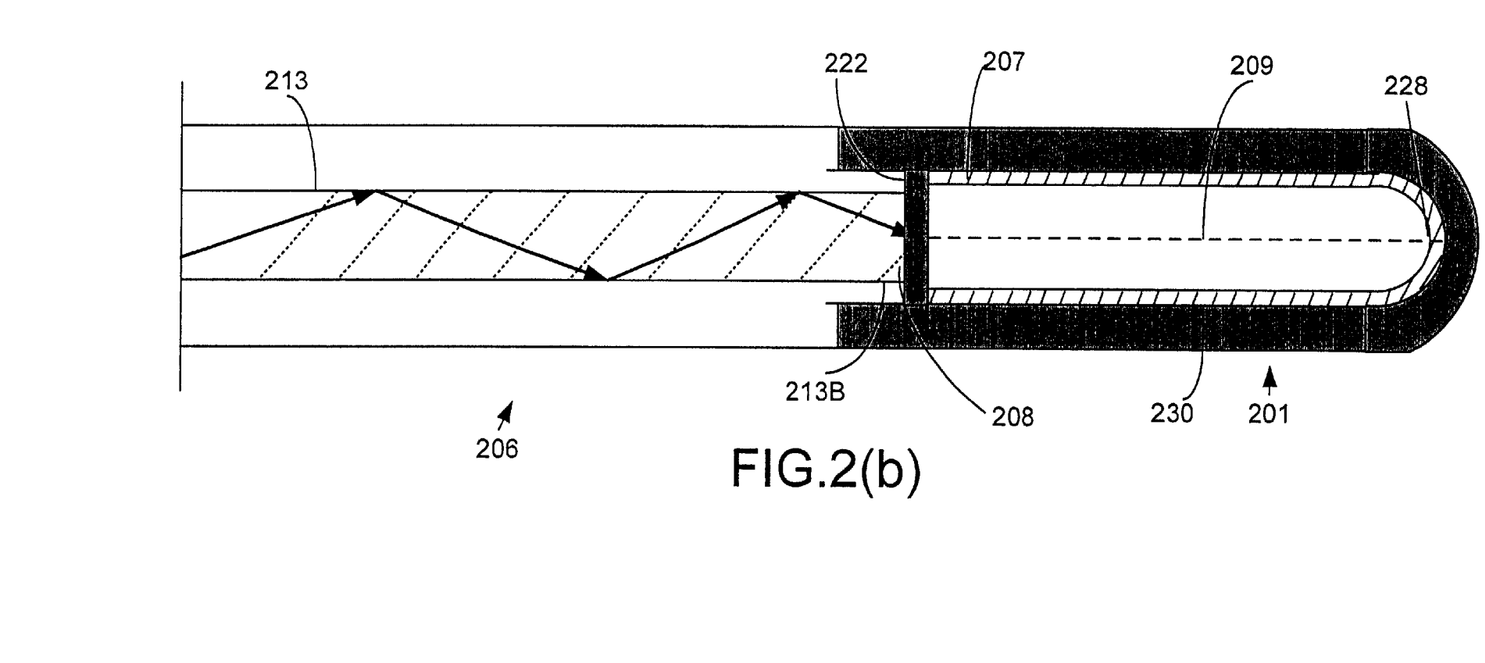
FIG. 2(b) provides an enlarged view of the radiation generator assembly, and the distal end of the probe assembly, constructed in accordance with the present invention.

FIGS. 2(a) and 2(b) show a diagrammatic view of one embodiment of the therapeutic radiation source apparatus 200 constructed according to the present invention. In the embodiment illustrated in FIG. 2(a), the apparatus 200 includes a laser source 204, a probe assembly 206, and a radiation generator assembly 201. The radiation generator assembly 201 includes an electron source 208 that generates an electron beam along a beam path 209, and a target assembly 210 positioned in the beam path. In the illustrated embodiment, a high voltage power supply 212 is also provided. The probe assembly 206 couples both the laser source 204 and the high voltage power supply 212 to the target assembly 210. FIG. 2(a) provides an overall view of the therapeutic radiation source 200, whereas FIG. 2(b) provides an enlarged view of 1) the radiation generator assembly 201, and 2) the distal end of the probe assembly 206.

Referring to both FIGS. 2(a) and 2(b), the radiation generator assembly 201, which can be for example 0.5 to 2 cm in length, extends from the end of the probe assembly 206 and includes a capsule 230 which encloses the target assembly and the electron source. According to one embodiment, the radiation generator assembly 201 is rigid in nature and generally cylindrical in shape. In this embodiment the cylindrical capsule 230 enclosing the radiation generator assembly 201 can be considered to provide a substantially rigid housing for the electron source 208. In one embodiment, the electron source 208 and the target assembly 210 is disposed within the capsule 230, with the thermionic cathode disposed at an input end of the capsule 230, and the target assembly 210 disposed at an output end of the housing 230.

The electron source 208 includes a thermionic cathode 222 having an electron emissive surface. The thermionic cathode 222 has an electron emissive surface, and is typically formed of a metallic material. Suitable metallic materials forming the cathode 222 may include tungsten, thoriated tungsten, other tungsten alloys, thoriated rhenium, and tantalum. In one embodiment, the cathode 222 may be formed by depositing a layer of electron emissive material on a base material, so that an electron emissive surface is formed thereon. By way of example, the base material may be formed from one or more metallic materials, including but not limited to Group VI metals such as tungsten, and Group II metals such as barium. In one form, the layer of electron emissive material may be formed from materials including, but not limited to, aluminum tungstate and scandium tungstate. The thermionic cathode 222 may also be an oxide coated cathode, where a coating of the mixed oxides of barium and strontium, by way of example, may be applied to a metallic base, such as nickel or a nickel alloy. The metallic base may be made of other materials, including Group VI metals such as tungsten.

The target assembly 210 preferably includes a target element 228 spaced apart from and opposite the electron emissive surface of the thermionic cathode 222, where the target element 228 has at least one radiation emissive element adapted to emit therapeutic radiation in response to incident accelerated electrons from the electron emissive surface of the thermionic cathode 222. In a preferred embodiment, the emitted therapeutic radiation consists of x-rays, however it should be noted that the scope of this invention is not limited to x-rays, and other forms of therapeutic radiation may also be generated.

In one embodiment, the target element 228 is a small beryllium (Be) window, coated on the side exposed to the incident electron beam with a thin film or layer of a high-Z, x-ray emissive element, such as tungsten (W), uranium (U) or gold (Au). By way of example, when the electrons are accelerated to 30 keV-, a 2 micron thick gold layer absorbs substantially all of the incident electrons, while transmitting approximately 95% of any 30 keV-, 88% of any 20 keV-, and 83% of any 10 keV-x-rays generated in that layer. In this embodiment, the beryllium target element 228 is 0.5 mm thick. With this configuration, 95% of the x-rays generated in directions normal to and toward the target element 228, and having passed through the gold layer, are then transmitted through the beryllium window and outward at the distal end of the probe assembly 206. In another embodiment, the target can be deposited on an x-ray opaque substrate at the distal end, and the x-ray beam would be formed in an annular shape.

In some forms of the invention, the target element 228 may include a multiple layer film, where the differing layers may have different emission characteristics. By way of example, the first layer may have an emission versus energy peak at a relatively low energy, and the second underlying layer may have an emission versus energy peak at a relatively high energy. With this form of the invention, a low energy electron beam may be used to generate x-rays in the first layer, to achieve a first radiation characteristic, and high energy electrons may be used to penetrate through to the underlying layer, to achieve a second radiation characteristic.

X-rays are generated in the target assembly in accordance with pre-selected beam voltage, current, and target element composition. The generated x-rays pass through the beryllium target substrate with minimized loss in energy. As an alternative to beryllium, the target substrate may be made of carbon, ceramic such as boron nitride, or other suitable material which permits x-rays to pass with a minimum loss of energy. An optimal material for target substrate is carbon in its diamond form, since that material is an excellent heat conductor. Using these parameters, the resultant x-rays have sufficient energy to penetrate into soft tissues to a depth of a centimeter or more, the exact depth dependent upon the x-ray energy distribution.

The invention also features means for establishing an accelerating electric field. In one embodiment, the means for establishing an accelerating electric field may be the high voltage power supply 212. The high voltage power supply 212 may establish an acceleration potential difference between the thermionic cathode 222 and the grounded target element 228, so that electrons emitted from the thermionic cathode 222 are accelerated toward the target element 228, and an electron beam is generated. The electron beam is preferably thin (e.g. 1 mm or less in diameter), and is established along a beam path 209 along a nominally straight reference axis that extends to the target assembly 210. The target assembly 210 is positioned in the beam path 209. The distance from the electron source 208 to the target assembly 210 is preferably less than 2 mm.

The capsule 230 defines a substantially evacuated interior region extending along the beam axis 209, between the thermionic cathode 222 at the input end of the capsule 230 and the target assembly 210 at the output end of the housing 230. The external surface of the assembly is electrically conductive. According to a preferred embodiment, the radiation generator assembly 201 is hermetically sealed to the end of the probe assembly, and evacuated. According to another embodiment, the entire probe assembly 206 is evacuated.

In optically-driven, miniaturized therapeutic radiation sources, such as the devices disclosed in U.S. Pat. No. 5,428,658, and in the '561 application, the interior surface of the capsule 230 is typically lined with an electrical insulator. In contrast, in the present invention the interior surface is coated with a layer 207 of semiconductor coating. The layer 207 of weakly conductive or semiconductive coating serves to prevent localized high electric field regions or "spikes" within the accelerating region inside the capsule 230, thereby substantially reducing the chances of electrical breakdown within the vacuum inside the capsule 230. The layer 207 of weakly conductive or semiconductive coating also substantially reduces the chances of the secondary emissions from electrons striking the inner wall of the capsule 230 from causing a avalanche that eventually leads to an electrical breakdown. The coating also ensures that the electron beam is not deflected off the target by chargeup effects on the insulator wall.

The present invention features an optically-driven, high efficiency therapeutic radiation source that maintains a substantially uniform voltage gradient within the evacuated region between the electron source and the target. The layer 207 of weakly conductive or semiconductive coating allows a substantially smooth voltage gradient to be maintained between a predetermined maximum value of the accelerating voltage and ground potential. The layer 207 of weakly conductive or semiconductive coating also serves to screen the thermionic cathode's "triple junction point," i.e. the junction between the cathode, housing wall, and vacuum, from high electric fields, thus preventing electron field emission and subsequent high voltage breakdown.

The probe assembly 206 couples the laser source 204 and the high voltage power supply 212 to the target assembly 210. In the illustrated embodiment, the probe assembly 206 includes a flexible, electrically conductive catheter 205 extending along a probe axis between a proximal end and a distal end of the catheter 205. The probe assembly 206 includes optical delivery structure 213 having an originating end 213A and a terminating end 213B. The terminating end 213B of the optical delivery structure 213 is affixed to the radiation generator assembly 201.

In a preferred embodiment, the optical delivery structure 213 is a flexible fiber optical cable. In this embodiment, the flexible catheter 205 that encloses the fiber optical cable 213 is a small-diameter, flexible, metallic outer tube. In this embodiment, the target assembly 210 includes an electrically conductive outer surface. Preferably, both the metallic tube 205 and the target element 228 are set at ground potential, in order to reduce the shock hazard of the device. In one embodiment, the fiber optical cable has a diameter of about 200 microns, and the flexible metallic tube 205 has a diameter of about 1.4 mm.

In a preferred embodiment, the fiber optic cable 213 includes an electrically conductive outer surface. For example, the outer surface of the fiber optic cable 213 may be made conductive by applying an electrically conductive coating. The electrically conductive outer surface of the fiber optic cable 213 provides a connection to the thermionic cathode 222 from the high voltage power supply 212. In this embodiment, the radiation generator assembly 201 also has an electrically conductive outer surface. Preferably, both the flexible metallic sheath 205 and the outer conductive surface of the radiation generator assembly 201 are set at ground potential, in order to reduce the shock hazard of the device. The flexible sheath 205 couples a ground return from the target element 228 to the high voltage power supply 212, thereby establishing a high voltage field between the thermionic cathode 222 and the target element 228. In an exemplary embodiment, the fiber optic cable 213 may have a diameter of about 200 microns, and the flexible metallic sheath 205 may have a diameter of about 1.4 mm. A layer of dielectric material provides insulation between the outer surface of the fiber optic cable 213 and the inner surface of the metallic sheath 205.

Getters may be positioned within the housing 230. The getters aid in creating and maintaining a vacuum condition of high quality. The getter has an activation temperature, after which it will react with stray gas molecules in the vacuum. It is desirable that the getter used have an activation temperature that is not so high that the x-ray device will be damaged when heated to the activation temperature.

The fiber optical cable 202 is adapted to transmit laser radiation, generated by the laser source 204 (shown in FIG. 2(a)) and incident on the originating end of the fiber optical cable assembly, to the terminating end of the fiber optical cable assembly 213. The fiber optical cable 202 is also adapted to deliver a beam of the transmitted laser radiation to impinge upon the electron-emissive surface of the thermionic cathode 222. The beam of laser radiation must have a power level sufficient to heat at least a portion of the electron-emissive surface to an electron emitting temperature so as to cause thermionic emission of electrons from the surface.

The high voltage power supply 212 preferably satisfies three criteria: 1) small in size; 2) high efficiency, so as to enable the use of battery power; and 3) independently variable x-ray tube voltage and current, so as to enable the unit to be programmed for specific applications, and highly stable. Preferably, the power supply 212 includes selectively operable control means, including means for selectively and independently controlling the amplitude of the output voltage and the amplitude of the beam generator current. A high-frequency, switch-mode power converter can be used to meet these requirements. The most appropriate topology for generating low power and high voltage is a resonant voltage converter working in conjunction with a high voltage, Cockroft-Walton-type multiplier. Low-power dissipation, switch-mode power-supply controller-integrated circuits (IC) are currently available for controlling such topologies with few ancillary components. A more detailed description of the power supply 212 is provided in U.S. Pat. Nos. 5,153,900 and 5,428,658.

In operation, the laser beam shining down the fiber optic cable 213 impinges upon the surface of the thermionic cathode 222, and rapidly heats the surface to an electron emitting temperature, below the melting point of the metallic cathode 222. Once the thermionic cathode reaches the electron emitting temperature, electrons are thermionically emitted from the surface. The high voltage field between the cathode 222 and the target element 228 (shown in FIGS. 3 and 4) accelerates these electrons, thereby forcing them to strike the surface of the target element 228 and produce x-rays. In one embodiment of the invention, a Nd:YAG laser was coupled into a SiO2 optical fiber having a diameter of 400 microns. A 20 kV power supply was used, and a thermionic cathode made of tungsten was used. The power required to heat the electron emissive surface of the cathode 222 so as to generate over 100 $\mu$A of electron current was only between about 0.1 Watts to about 3.0 Watts. In another example, an infrared diode laser was used to achieve about 100 $\mu$A of electron current with only 180 mW of power. The weakly conductive or semiconductive coating 207 preferably allows the voltage gradient within the evacuated capsule 230 to be controlled, so that a substantially uniform electric field is maintained within the accelerating region.

Figure 3A:
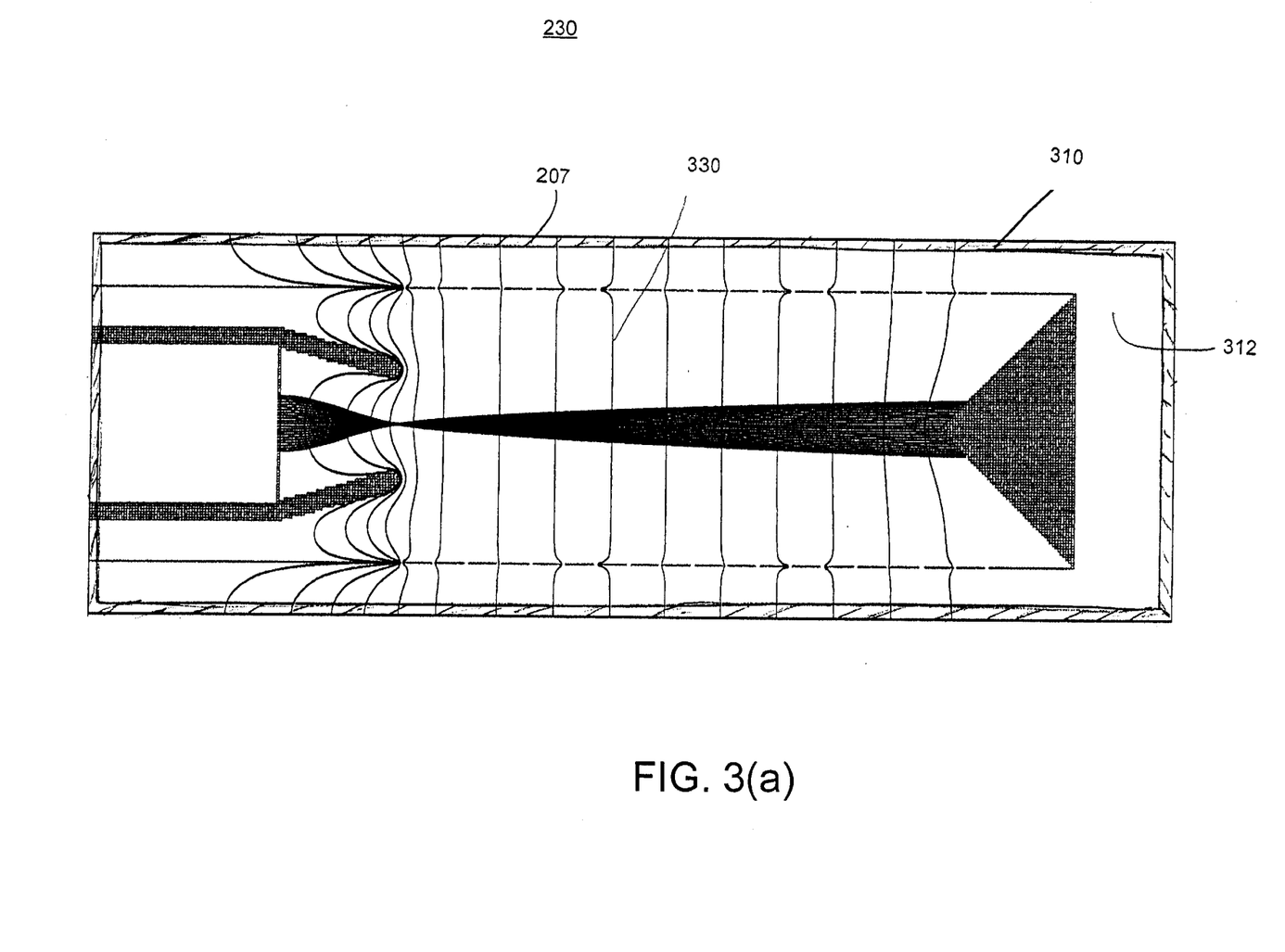
FIG. 3(a) illustrates an enlarged view of the field lines for the voltage gradient within an evacuated capsule.

FIG. 3(a) illustrates in more detail an enlarged view of the interior of the substantially rigid capsule 230. In particular, FIG. 3(a) illustrates the electromagnetic field lines 330 within the interior of the capsule 230, showing a substantially smooth voltage gradient across the evacuated region within the capsule. As seen from FIG. 3(a), the capsule 230 has an interior surface 310 that defines a hollow, evacuated region 312. As mentioned earlier in connection with FIGS. 2(a) and 2(b), the high voltage power supply (shown in FIGS. 2(a) and 2(b)) provides an accelerating voltage for accelerating the electrons emitted from the electron source toward the target element. Because it is safer to maintain the target element at ground potential, the thermionic cathode may be negatively biased, so that the target element is maintained at a net positive voltage with respect to the thermionic cathode. The accelerating voltage has a predetermined maximum value, typically about 90 keV.

The hollow interior surface 310 is coated with a layer 207 of weakly conductive or semiconductive coating. This is because the weakly conductive or semiconductive coating allows for voltage gradient control within the evacuated region. In other words, the weakly conductive or semiconductive coating 207 allows a substantially smooth voltage gradient to be maintained between the predetermined maximum value of the accelerating voltage, and the ground potential, as illustrated by the voltage gradient field lines 330 in FIG. 3. The coating 207 may be made of weakly conductive or semiconductive materials, including but not limited to chromium sesquioxide, vanadium pentoxide, or ion implanted metals such as platinum.

The high-resistance coating 207, which is weakly conductive or semiconductive, and which is applied to the interior surface 310 of the capsule 230 in the optically-driven, miniaturized therapeutic radiation source of the present invention, improves the ability of the therapeutic source 200 to withstand high acceleration voltages, without breakdown. It also greatly enhances the x-ray output and stability, as the efficiency in propagating the electrons to the target is greatly increased. This is in contrast to prior art devices, such as disclosed in U.S. Pat. No. 5,428,658, and to the miniaturized, optically-driven therapeutic radiation sources, such as disclosed for example in the '561 application. These devices contained a film of insulating material on the inner surface of the evacuated capsule, rather than a high resistance, semiconductive (or weakly conductive) coating, so that no control was possible over the voltage gradient within the evacuated region.

As mentioned earlier, the reliability of the vacuum within the capsule 230 is limited by the operational risk of an unpredictable "sparking" or "arcing" between the electrodes, when the insulating capability of the evacuated region 312 is suddenly lost, and electrical breakdown is said to have occurred. Because of such practical limitation of the insulating capability of the vacuum, localized high voltage gradient regions or "spikes" may be caused. Such spikes may occur in the accelerating region within the evacuated capsule 230, as the emitted electrons are accelerated toward the target. In order to avoid such spikes in the electric field within the evacuated region 312, it is preferable that the inner surface 310 of the capsule 230 be lined with a weakly conductive or semiconductive material that can directly control the electric field. The present invention provides such as low dielectric constant material in the form of the resistive layer 207 of weakly conductive or semiconductive coating.

There is a wide range of physical phenomena, such as electrode heating and thermal diffusion processes, and electron emissions, which contribute to the performance of the vacuum gap and its ability to withstand electrical breakdown. The breakdown voltage depends on a number of parameters, including but not limited to electrode material and geometry, surface preparation and geometry, vacuum quality, and vacuum gap spacing. In particular, the breakdown voltage is typically a function of the dielectric constant of the material forming the capsule 230. It is preferable that the material forming the capsule 230 have a high dielectric strength, in order to withstand a large electrical field without breakdown. Preferably, the dielectric strength of the capsule material, which may be a ceramic by way of example, is at least 100 kV/mm. The ceramic material that forms the capsule 230 may include, but is not limited to, glass, boron nitride, sapphire, fused silica, and diamond.

The layer 207 of weakly conductive or semiconductive coating also serves to reduce secondary emissions from the interior surface 310. Secondary emissions of electrons hitting the walls of the capsule enclosing the accelerating region may cause an avalanche, eventually leading to a breakdown. Such an avalanche is likely to happen when the inner surface 310 of the capsule 230 is lined with an insulator material, for example a material having a secondary emission coefficient>3. The semiconductive coating 207, which in one exemplary embodiment may have a secondary emission coefficient<1, serves to prevent such an avalanche. Also, charge-up, and subsequent electric field intensification and breakdown, are eliminated by draining the charge through the weakly conductive or semiconductive layer.

Figure 3B:
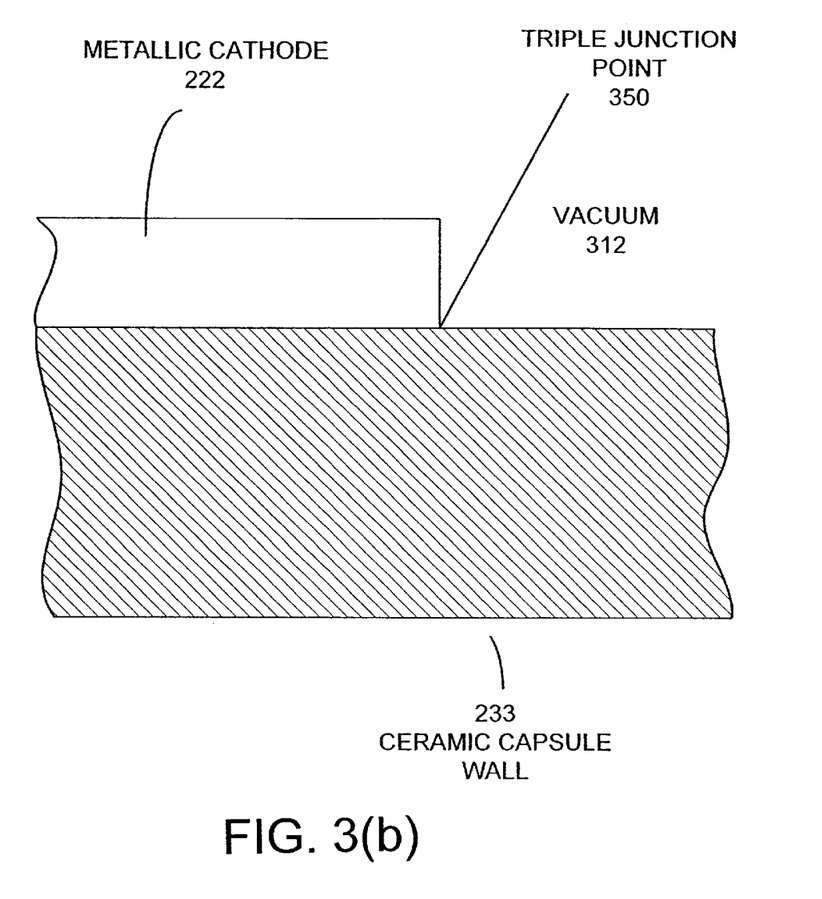
FIG. 3(b) illustrates the triple junction point of the thermionic cathode used in the present invention.

FIG. 3(b) illustrates the thermionic cathode's triple junction point 350. The weaker the electric field at the cathode, the more imperfections or irregularities can be tolerated on the surface of the thermionic cathode, without risking flashover. The triple junction point 350 may be screened from the high electrical field between the target element 228 and the cathode 222 by the weakly conductive or semiconductive coating 207, thereby substantially reducing the chances of electrical flashover.

In the present invention, the electric field within the evacuated accelerating region is controlled by a resistive, weakly conductive or semiconductive coating 207 on the inner surface of the capsule enclosing the x-ray generator assembly. The weakly conductive or semiconductive coating 207 generates a controlled voltage gradient across the vacuum within the capsule 230. Also, the weakly conductive or semiconductive coating 207 is adapted to reduce the strength of the electric field near the triple junction point of the thermionic cathode, thereby reducing the chances of electrical flashover. Finally, the weakly conductive or semiconductive coating 207 prevents the amplification of the secondary emissions of electrons that hit the inner wall of the capsule 230 by absorbing the emitted electrons, thereby preventing an avalanche of emissions that could lead to electrical breakdown. For these reasons, the chances for electrical flashover or electric breakdown within the evacuated capsule 230 is substantially reduced, thereby providing a significant advantage over optically driven therapeutic radiation sources in which the inner surface of the capsule 230 is lined with an insulator material. Also, the weakly conductive or semiconductive coating increases the x-ray production efficiency and stability by ensuring that the electrons emitted from the cathode proceed directly to the target, thereby maximizing the probability that they will hit the x-ray target, and maximizing the electrons' kinetic energy as they impact the target.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A therapeutic radiation source, comprising:
   A. an optical source;
   B. a probe assembly, including an optical delivery structure having a proximal end and a distal end, said optical delivery structure being adapted for transmitting optical radiation incident on said proximal end to said distal end, said optical delivery structure being adapted for directing a beam of optical radiation transmitted therethrough to impinge upon a surface of said thermionic cathode;
   C. a radiation generator assembly coupled to said probe assembly, including:
      a. an electron source, responsive to optical radiation transmitted to said distal end of said optical delivery structure, for generating an electron beam along a beam path, said electron source including a thermionic cathode having an electron emissive surface; and
      b. a target element positioned in said beam path, said target element including at least one x-ray emissive material adapted to emit x-rays in response to incident accelerated electrons from said electron source; and
      c. a substantially rigid capsule enclosing said electron source and said target element, wherein said capsule defines a substantially evacuated interior region extending along a beam axis between said thermionic cathode at a proximal end of said capsule and said target element at a distal end of said capsule;
   D. means for providing an accelerating voltage between said electron source and said target element so as to establish an accelerating electric field which acts to accelerate electrons emitted from said electron source toward said target element, said accelerating voltage at said source having a preselected maximum value relative to a reference potential at said target element;
      wherein said beam of transmitted optical radiation has a power level sufficient to heat at least a portion of said surface to an electron emitting temperature so as to cause thermionic emission of electrons from said surface; and
      wherein the inner surface of said capsule is coated with a semiconductive coating to provide a substantially smooth voltage gradient within said capsule between said preselected maximum value and the reference potential.

2. A therapeutic radiation source according to claim 1, wherein said semiconductive coating comprises a weakly conductive coating.

3. A therapeutic radiation source according to claim 2, wherein said semiconductive coating is formed of an ion-implanted metal.

4. A therapeutic radiation source according to claim 1, whereby a surface resistivity of said inner surface of said capsule establishes a relatively low power dissipation.

5. A therapeutic radiation source according to claim 1, wherein the dielectric constant of said inner surface of said capsule is sufficiently small so as to prevent spikes in said accelerating electric field.

6. A therapeutic radiation source according to claim 1, wherein a secondary electron emission coefficient of said inner surface of said capsule is less than 1.

7. A therapeutic radiation source according to claim 1, wherein said semiconductive coating applied to said inner surface of said capsule is adapted to screen from electrical flashover a triple junction point of said thermionic cathode.

8. A therapeutic radiation source according to claim 1, wherein said optical source is a laser, and wherein said beam of optical radiation is substantially monochromatic and coherent.

9. A therapeutic radiation source according to claim 1, wherein said electron emissive surface of said thermionic cathode is formed of a metallic material.

10. A therapeutic radiation source according to claim 9, wherein said metallic material includes tungsten, thoriated tungsten, tungsten alloys, thoriated rhenium, and tantalum.

11. A therapeutic radiation source according to claim 1, wherein said electron beam is characterized by a current in the approximate range of about 1 nA to about 1 mA.

12. A therapeutic radiation source according to claim 1, wherein said electrons incident on said target element from said electron emissive surface are accelerated by said accelerating electric field to energies in the approximate range of 10 keV to 90 keV.

13. A therapeutic radiation source according to claim 1, wherein the means for establishing an accelerating voltage is a power supply having a first terminal and a second terminal, said power supply being electrically coupled to said x-ray generator assembly by way of said first and said second terminal.

14. A therapeutic radiation source according to claim 13, wherein said power supply further includes selectively operable control means for selectively controlling the amplitude of said output voltage, and wherein said power supply further includes selectively operable control means for selectively controlling the amplitude of said beam current.

15. A therapeutic radiation source according to claim 1, wherein said thermionic cathode includes a metallic base coated with an oxide.

16. A therapeutic radiation source according to claim 15, wherein said oxide includes barium oxide, strontium oxide, and calcium oxide, and said metallic base includes nickel.

17. A therapeutic radiation source according to claim 1, wherein said optical delivery structure includes a fiber optic cable.

18. A therapeutic radiation source according to claim 17, wherein said probe assembly includes a flexible, electrically conductive catheter enclosing said fiber optic cable.

19. A therapeutic radiation source according to claim 17, wherein said fiber optic cable includes an electrically conductive outer surface, said electrically conductive outer surface being adapted for electrically coupling said first terminal of said power supply to said thermionic cathode.

20. A therapeutic radiation source according to claim 1, wherein the power required to heat said electron emissive surface of said cathode so as to generate an electron beam forming a current of about 100 micro amps is between about 0.1 Watts to about 3.0 Watts.

21. A therapeutic radiation source, comprising:

A. an optical source;

B. a probe assembly, including an optical delivery structure having a proximal end and a distal end, said optical delivery structure being adapted for transmitting optical radiation incident on said proximal end to said distal end, said optical delivery structure being adapted for directing a beam of optical radiation transmitted therethrough to impinge upon a surface of said thermionic cathode;

C. a radiation generator assembly coupled to said probe assembly, including:

a. an electron source, responsive to optical radiation transmitted to said distal end of said optical delivery structure, for generating an electron beam along a beam path, said electron source including a thermionic cathode having an electron emissive surface; and    b. a target element positioned in said beam path, said target element including at least one x-ray emissive material adapted to emit x-rays in response to incident accelerated electrons from said electron source; and    c. a substantially rigid capsule enclosing said electron source and said target element, wherein said capsule defines a substantially evacuated interior region extending along a beam axis between said thermionic cathode at a proximal end of said capsule and said target element at a distal end of said capsule;

D. means for providing an accelerating voltage between said electron source and said target element so as to establish an accelerating electric field which acts to accelerate electrons emitted from said electron source toward said target element;

wherein said beam of transmitted optical radiation has a power level sufficient to heat at least a portion of said surface to an electron emitting temperature so as to cause thermionic emission of electrons from said surface; and    wherein the inner surface of said capsule is coated with a semiconductive coating to provide a substantially smooth voltage gradient within said capsule between said electron source and said target element.

22. A therapeutic radiation source according to claim 21, wherein said semiconductive coating comprises a weakly conductive coating.

23. A therapeutic radiation source according to claim 21, wherein said semiconductive coating is adapted to reduce secondary emissions of electrons striking said inner surface of said capsule.

24. A therapeutic radiation source according to claim 1, wherein said semiconductive coating is formed of a material selected from the group consisting of chromium sesquioxide, vanadium pentoxide, and platinum.

* * * * *